United States Patent [19]

Naylor et al.

[11] Patent Number: 4,943,578
[45] Date of Patent: Jul. 24, 1990

[54] PIPERAZINE COMPOUNDS

[75] Inventors: Alan Naylor; Duncan B. Judd, both of Ware; Dearg S. Brown, Middlesex, all of England

[73] Assignee: Glaxo Group Limited, London, United Kingdom

[21] Appl. No.: 355,335

[22] Filed: May 23, 1989

[30] Foreign Application Priority Data

May 23, 1988 [GB] United Kingdom ............... 8812179
Sep. 5, 1988 [GB] United Kingdom ............... 8820845

[51] Int. Cl.$^5$ .................. A61K 31/495; C07D 401/06; C07D 403/06
[52] U.S. Cl. ..................... 514/252; 514/255; 544/360; 544/367; 544/372; 544/386; 544/387
[58] Field of Search ............... 544/360, 372, 387, 367, 544/386; 514/252, 255

[56] References Cited

U.S. PATENT DOCUMENTS

| | | | |
|---|---|---|---|
| 3,184,463 | 5/1965 | Irikura et al. | 544/387 |
| 3,324,128 | 6/1967 | Irikura et al. | 544/387 |
| 3,347,860 | 10/1967 | Irikura et al. | 544/387 |
| 4,579,863 | 4/1986 | Horwell et al. | 514/422 |
| 4,705,781 | 11/1987 | Boast | 514/85 |

FOREIGN PATENT DOCUMENTS

| | | |
|---|---|---|
| 176309 | 4/1986 | European Pat. Off. . |
| 233793 | 8/1987 | European Pat. Off. . |
| 256890 | 2/1988 | European Pat. Off. . |
| 284359 | 9/1988 | European Pat. Off. ............ 544/387 |
| 8801131 | 2/1988 | Int'l Pat. Institute . |
| 67/2269 | 2/1967 | Japan . |

Primary Examiner—Cecilia Shen
Attorney, Agent, or Firm—Bacon & Thomas

[57] ABSTRACT

Compounds are disclosed of formula (I)

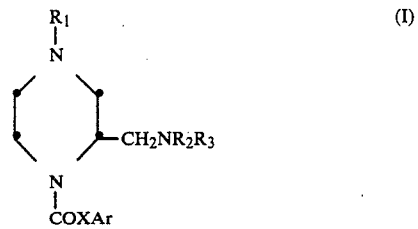

wherein
$R_1$ represents —$COR_4$, —$CO_2R_4$ or —$COCO_2R_4$ (where $R_4$ represents a hydrogen atom or an unsubstituted or substituted $C_{1-10}$ hydrocarbon moiety);
$R_2$ and $R_3$ are the same or different and are $C_{1-6}$alkyl or $C_{3-6}$alkenyl; or —$NR_2R_3$ forms a 5-membered (optionally containing an oxygen atom adjacent to the nitrogen) or 6-membered ring, which ring optionally contains one unit of unsaturation and which is unsubstituted or substituted by optionally substituted methylidene, —$COR_5$ (where $R_5$ represents $C_{1-6}$alkyl, —$OR_6$ or —$NHR_6$ and $R_6$ represents hydrogen, $C_{1-6}$alkyl, aryl, or ar($C_{1-6}$)alkyl, or N=$NOR_7$ (where $R_7$ represents $C_{1-6}$alkyl);
X represents a direct bond, —$CH_2$— or —$CH_2O$—;
Ar represents a substituted phenyl moiety;
and physiologically acceptable salts thereof.

The compounds are indicated as useful in the treatment of pain and cerebral ischaemia.

Processes and intermediates for their preparation and pharmaceutical compositions containing them are also disclosed.

10 Claims, No Drawings

PIPERAZINE COMPOUNDS

This invention relates to piperazine derivatives, to processes for their preparation, to pharmaceutical compositions containing them and to their medical use. In particular, the invention relates to compounds which act as agonists at kappa opioid receptors.

Compounds which are kappa opioid receptor agonists have been indicated in the art for the treatment of a number of conditions and have been described, for example, as analgesics, as diuretics and in the treatment of cerebral ischaemia. Opioid analgesia is generally throught to be mediated by either mu or kappa receptors in the brain (see, for example, Tyers M. B., *Br. J. Pharmacol*, (1980), 69, 503–512). Most existing clinically used opioid analgesics such as morphine and codeine act as mu-receptor agonists. However, these compounds have undesirable and potentially dangerous dependence-forming side effects. There is thus a need for a strong analgesic with low dependence liability and a compound which is a selective kappa-receptor agonist would fulfil such a role.

Cerebral ischaemia or lack of blood flow in the brain, may result from a number of conditions, including, for example, stroke, head injuries or brain tumour. The resulting lack of oxygen to the brain cells causes neuronal damage and depending on the region of the brain involved, death or permanent disability may occur.

We have now found a novel group of piperazine derivatives which are selective kappa opioid receptor agonists. These compounds are therefore of interest in the treatment of conditions where the underlying aetiology indicates that treatment with a kappa opioid receptor agonist would be beneficial.

Thus, the present invention provides compounds of formula (I):

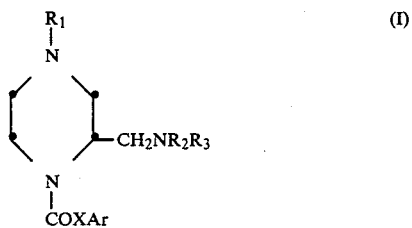

wherein
$R_1$ represents —$COR_4$, —$CO_2R_4$ or —$COCO_2R_4$ (where $R_4$ is a hydrogen atom or an unsubstituted or substituted $C_{1-10}$ hydrocarbon moiety);
$R_2$ and $R_3$ are the same or different and are $C_{1-6}$ alkyl or $C_{3-6}$ alkenyl; or —$NR_2R_3$ forms a 5-membered (optionally containing an oxygen atom adjacent to the nitrogen) or a 6-membered ring, which ring optionally contains one unit of unsaturation and which is unsubstituted or substituted by optionally substituted methylidene,
—$COR_5$ (where $R_5$ represents $C_{1-6}$ alkyl, $OR_6$ or —$NHR_6$, and $R_6$ represents hydrogen, $C_{1-6}$ alkyl, aryl, ar($C_{1-6}$)alkyl) or =$NOR_7$ (where $R_7$ represents $C_{1-6}$alkyl);
X represents a direct bond, —$CH_2$— or —$CH_2O$—;
Ar represents a substituted phenyl moiety;
and physiologically acceptable salts thereof.

As used herein, the term 'hydrocarbon moiety' means any non-aromatic moiety containing only carbon and hydrogen atoms. This moiety may be cyclic, acyclic or a combination thereof and may optionally contain one or more units of unsaturation. Where the hydrocarbon moiety contains one or more units of unsaturation it may be conjugated or unconjugated and may conveniently be, for example a $C_{2-6}$, preferably $C_{2-3}$alkenyl group such as ethenyl.

Conveniently the hydrocarbon moiety is an alkyl group containing from 1 to 6 carbon atoms, preferably from 1 to 3 carbon atoms, which is unsubstituted or substituted by any substituent (other than an aromatic substituent) conventional in the art. Suitable substituents include, for example, electron-withdrawing substituents such as halogen (for example fluorine) or —$CF_3$.

Where the hydrocarbon moiety is a cyclic group this is conveniently $C_{3-10}$ cycloalkyl, preferably $C_{3-7}$ cycloalkyl, for example cyclopropyl, cyclobutyl, cyclopentyl, cyclohexyl or cycloheptyl.

Where the hydrocarbon moiety contains a combination of acyclic and cyclic groups this may conveniently be a cycloalkylalkyl group. The alkyl moiety of such a group is conveniently a $C_{1-4}$ moiety and may be, for example, a methyl or ethyl moiety. The cycloalkyl moiety of a cycloalkylalkyl group conveniently contains from 3 to 7 carbon atoms. Examples of suitable groups include cyclopropylmethyl, cyclobutylmethyl, cyclopentylmethyl, cyclohexylmethyl or cycloheptylmethyl.

As used herein, a $C_{1-6}$ alkyl group or the alkyl moiety of an ar($C_{1-6}$)alkyl or cycloalkylalkyl group may be straight or branched chain and is conveniently $C_{1-4}$ alkyl, for example methyl, ethyl, propyl or butyl. An aryl group or the aryl moiety of an ar($C_{1-6}$)alkyl group is preferably phenyl.

An alkenyl group may be a straight or branched chain group containing one or more units of unsaturation, which units of unsaturation may be conjugated or unconjugated. Where $R_2$ and/or $R_3$ in the compounds of formula (I) represents an alkenyl group, it will be appreciated that no double bond will be attached to the carbon atom adjacent to the nitrogen.

The term 'optionally substituted methylidene' as used herein includes methylidene substituted by any substituent conventional in the art. In the compounds of formula (I), the methylidene group may conveniently be substituted to form a conjugated system. Suitable substituents which form a conjugated system with the methylidene double bond include, for example, nitrile, phenyl, carboxyl and amido. Alternatively the methylidene group may conveniently be substituted by, for example, a $C_{1-6}$ alkyl group, an ar($C_{1-6}$)alkyl group such as phenethyl, a $C_{1-6}$ hydroxyalkyl group such as hydroxymethyl, a $C_{1-6}$ carboxyalkyl group such as methoxycarbonylethyl or $C_{1-6}$ amidoalkyl group such as aminocarbonylethyl.

Where —$NR_2R_3$ forms a substituted or unsubstituted 5 or 6-membered ring optionally containing one unit of unsaturation this may be, for example, a substituted or unsubstituted pyrrolidine, isoxazolidine or tetrahydropyridine ring. It will be appreciated that where the ring formed by —$NR_2R_3$ contains a unit of unsaturation, this will not be attached to a carbon atom adjacent to the nitrogen atom.

The term 'a substituted phenyl moiety' as used herein is a phenyl moiety substituted by one or more conventional substituents in the art, which substituents may form a second ring optionally containing one or more units of unsaturation. In the compounds of formula (I), Ar conveniently represents a phenyl moiety which is substituted by one or more $C_{1-6}$ alkyl groups or electron-withdrawing substituents, or in which two adjacent substituents form a second ring. Suitable electron-withdrawing substituents include, for example, halogen (for example, fluorine, chlorine or bromine), —$CF_3$ or —$NO_2$. Where two substituents on the phenyl ring form a second ring, Ar may suitably represent naphthyl, for example 1-naphthyl or 2-naphthyl. Ar is preferably substituted at the meta and/or para positions on the phenyl ring by one or more halogens, for example chlorine and is typically a 3,4-dichlorophenyl moiety.

In one preferred class of compounds of formula (I), $R_1$ represents —$COR_4$.

In a further preferred class of compounds of formula (I), $R_1$ represents —$CO_2R_4$.

In another preferred class of compounds of formula (I), $R_1$ represents —$COCO_2R_4$.

$R_4$ conveniently represents a $C_{1-6}$ (preferably $C_{1-3}$) alkyl group such as methyl, ethyl or propyl or a $C_{2-6}$ (preferably $C_{2-3}$) alkenyl group such as ethenyl.

Conveniently $R_1$ may be, for example, a group —CHO, —$COCH_3$, —$COCH_2CH_3$, —$COCH_2CH_2CH_3$, —$COCH=CH_2$, —$CO_2CH_3$, —$CO_2CH_2CH_2CH_3$, —$CO_2CH_2CH_2CH_3$ or —$COCO_2CH_3$.

$R_2$ and $R_3$ may each independently represent a $C_{1-6}$ alkyl group such as methyl, or —$NR_2R_3$ may suitably represent a substituted or unsubstituted pyrrolidine or tetrahydropyridine ring.

—$NR_2R_3$ conveniently represents a substituted or unsubstituted pyrrolidine or tetrahydropyridine ring. Where —$NR_2R_3$ represents a substituted ring, the substituent is preferably attached to the carbon atom $\beta$ to the nitrogen atom.

In a preferred class of compounds of formula (I), —$NR_2R_3$ represents a pyrrolidine ring.

X preferably represents —$CH_2$—.

In a further preferred class of compounds of formula (I), Ar represents a halosubstituted phenyl moiety, in particular a chlorosubstituted phenyl moiety such as 3,4-dichlorophenyl.

A preferred class of compounds falling within the scope of formula (I) is that in which $R^1$ represents —$CO^2CH^3$, —$CO^2CH^2CH^3$, —$COCH_3$ or —$COCH_2CH_2CH_3$ or $COCH=CH_2$; —$NR_2R_3$ forms a substituted or more preferably an unsubstituted pyrrolidine or tetrahydropyridine ring; X represents —$CH_2$—; Ar represents halosubstituted phenyl; and physiologically acceptable salts thereof. Particularly preferred compounds falling within this class are those in which Ar represents chlorosubstituted phenyl.

Preferred compounds according to the invention include:
4-Acetyl-1-[(3,4-dichlorophenyl)acetyl]-2-(1-pyrrolidinylmethyl) piperazine;
1-[(3,4-Dichlorophenyl)acetyl]-4-(1-oxo-2-propenyl)-2-(1-pyrrolidinylmethyl)piperazine;
1-[(3,4-Dichlorophenyl)acetyl]-4-(1-oxopropyl)-2-(1-pyrrolidinylmethyl)piperazine;
4-Acetyl-1-[(3,4-dichlorophenyl)acetyl]-2-[(1,2,3,6-tetrahydro-1-pyridyl)methyl]piperazine;
Ethyl 4-[(3,4-dichlorophenyl)acetyl]-3-(1-pyrrolidinylmethyl)-1-piperazinecarboxylate;
Methyl 4-[(3,4-dichlorophenyl)acetyl]-3-[(1,2,3,6-tetrahydro-1-pyridinyl)methyl]-1-piperazinecarboxylate
and physiologically acceptable salts thereof.

A particularly preferred compound according to the invention is:
Methyl 4-[(3,4-dichlorophenyl)acetyl]-3-(1-pyrrolidinylmethyl)-1-piperazinecarboxylate
and its physiologically acceptable salts.

Compounds of formula (I) contain at least one chiral centre and may exist in more than one stereoisomeric form. The invention includes within its scope all enantiomers, diastereomers and mixtures thereof. The invention also embraces all geometric isomers of compounds of formula (I).

The preferred stereoisomeric form of the compounds of formula (I) are those represented by the formula (Ia):

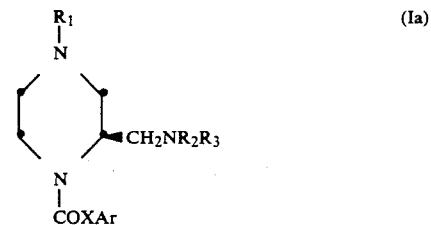

(Ia)

wherein $R_1$, $R_2$, $R_3$, X and Ar are as defined for formula (I).

Suitable physiologically acceptable salts are those conventionally known in the art. Examples of physiologically acceptable salts include acid addition salts formed with inorganic acid, such as hydrochlorides, hydrobromides, phosphates and sulphates, and with organic acids, for example tartrates, maleates, fumarates, succinates and sulphonates. Other salts which are not pharmaceutically acceptable may be useful in the preparation of compounds of formula (I) and these form a further part of the invention.

Compounds of the invention may readily be isolated in association with solvent molecules by crystalliation from or evaporation of an appropriate solvent. It is intended to include such solvates within the scope of the present invention.

Compounds falling within formula (I) have been shown to have analgesic activity using standard laboratory animal tests such as the mouse abdominal constriction test (M. B. Tyers, *Brit. J. Pharmacol*, 1980, 69, 503–512) or the rat paw pressure test. Furthermore, their kappa receptor activity has been demonstrated in vitro in the field stimulated rabbit vas deferens preparation using the procedure described by A. G. Hayes and A. Kelly, *Eur. J. Pharmacol* 110, 317–322 (1985). Compounds of the invention and their physiologically acceptable salts thus possess analgesic activity with the potential for low dependence liability and are therefore useful in the relief of pain.

Compounds of the invention are also of value in protecting against neuronal damage resulting from cerebral ischaemia which may be demonstrated for example in standard laboratory bilateral carotid occlusion models. Thus, compounds of the invention and their physiologically acceptable salts are also useful in treating or relieving the effects of cerebral ischaemia.

Accordingly, the invention also provides a compound of formula (I) or a physiologically acceptable salt thereof for use in medicine, in particular for the treatment of conditions where kappa agonists are indicated, (for example as analgesics and in the treatment of cerebral ischaemia).

In an alternative or further aspect there is provided a method of treatment of a mammal, including man, comprising administration of an effective amount of a compound of formula (I) or a physiologically acceptable salt thereof in particular in the treatment of conditions where the use of a kappa receptor agonist is indicated.

The invention also provides the use of a compound of formula (I) or a physiologically acceptable salt thereof for the manufacture of a medicament for the treatment of conditions where kappa receptor agonists are indicated.

It will be appreciated that compounds of the invention will primarily be of use in the alleviation of established symptoms but prophylaxis is not excluded.

Compounds of the invention may be administered as the raw chemical but the active ingredient is preferably presented as a pharmaceutical formulation. The active ingredient may conveniently be presented in unit dose form.

According to another aspect, the invention provides a pharmaceutical composition comprising at least one compound of formula (I) or a physiologically acceptable salt thereof and formulated for administration by any convenient route conventional in the art. Such compositions are preferably in a form adapted for use in medicine, in particular human medicine and can conveniently be formulated in conventional manner using one or more pharmaceutically acceptable carriers or excipients. Compounds according to the invention may conveniently be formulated for oral or parenteral administration.

For oral administration, the pharmaceutical compositions may take the form of, for example, tablets or capsules prepared by conventional means with pharmaceutically acceptable excipients such as binding agents (for example pregelatinised maize starch, polyvinylpyrrolidone or hydroxypropyl methylcellulose); fillers (for example lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example methyl or propyl-p-hydroxybenzoates or sorbic acid).

The compounds of the invention may be formulated for parenteral administration by injection conveniently intravenous or subcutaneous injection, for example by bolus injection or continuous intravenous infusion. Where the compounds are administered by continuous intravenous infusion this is conveniently sequential to a bolus injection. Formulations for injection may be presented in unit dosage form, for example, in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, for example sterile pyrogen-free water, before use.

It will be appreciated that the precise dose administered will depend on the age and condition of the patient, the particular compound used, and the frequency and route of administration. The compounds may be administered in single or divided doses and may be administered one or more times, for example 1 to 4 times, per day.

A proposed dose of the compounds of the invention for the relief of pain or the treatment of cerebral ischaemia is 0.01 to 100 mg/kg body weight, preferably 0.01 to 10 mg/kg body weight, most preferably 0.1 to 10 mg/kg body weight per day.

According to another aspect of the invention compounds of formula (I) and their physiologically acceptable salts may be prepared by the general method outlined below in which $R_1$, $R_2$, $R_3$, X and Ar are as defined for formula (I) unless otherwise indicated. It will be appreciated that in the method for preparing compounds of formula (I) given below it may be necessary or desirble to protect one or more sensitive groups in the molecule to prevent undesirable side reactions. Thus a reaction step comprising deprotection of a protected derivative of a compound of the invention may be required subsequent to the process described below. Protection and deprotection may be effected using conventional procedures as described, for example, in 'Protective Groups in Organic Synthesis', T. W. Greene (John Wiley & Sons, 1981).

According to one general process (A) compounds of formula (I) may be prepared by reacting a compound of formula (II)

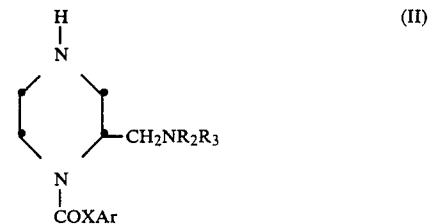

with a reagent serving to introduce the group —$R_1$.

Thus, for example, compounds of formula (I) may be prepared by reacting a compound of formula (II) with an acid $R_8CO_2H$ wherein $R_8$ represents $R_4$, $R_4O—$ or $R_4O_2C—$ as appropriate or an acylating agent corresponding thereto.

Suitable acylating agents corresponding to the acid $R_8CO_2H$ which may conveniently be used include, for example, acid halides (for example acid chlorides), alkyl esters (for example, methyl or ethyl esters) and mixed anhydrides. Such acylating agents may conveniently be prepared from the acid itself by conventional methods.

The reaction of a compound of formula (II) with an acid $R_8CO_2H$ is desirably effected in the presence of a coupling agent such as carbonyldiimidazole, dicyclohexylcarbodiimide or diphenylphosphoryl azide in a suitable reaction medium and conveniently at a temperature of from $-50°$ to $+50°$ C., preferably at ambient temperature. The reaction may be effected in a suitable reaction medium such as an ether (for example tetrahydrofuran), a haloalkane (for example, dichloromethane), a nitrile (for example acetonitrile), an amide (for example dimethylformamide), or mixtures thereof.

The reaction of a compound of formula (II) with an acylating agent corresponding to the acid $R_8CO_2H$ may conveniently be effected in a reaction medium and at a temperature as described above and optionally in the presence of a base. Suitable bases which may be employed include, for example, organic bases such as pyridine or triethylamine or inorganic bases such as calcium carbonate or sodium bicarbonate.

Compounds of formula (II) may conveniently be prepared from readily obtained starting materials by methods known in the art.

For example compounds of formula (II) may conveniently be prepared from compounds of formula (III)

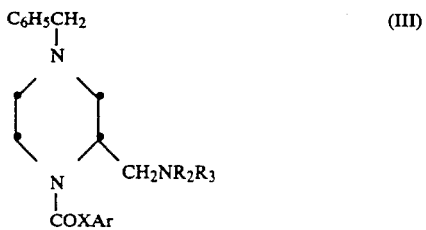

by removal of the benzyl group by conventional methods such as hydrogenation. Compounds of formula (III) may in turn be prepared by reductive amination of a compound of formula (IV)

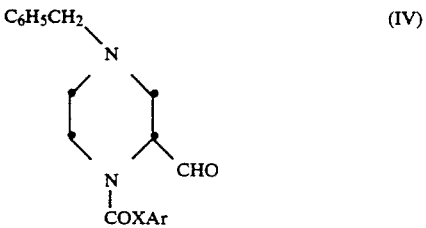

with an amine $R_2R_3NH$ in the presence of a suitable reducing agent according to the method of process (C) below.

Compounds of formula (IV) may be prepared, for example, from compounds of formula (V)

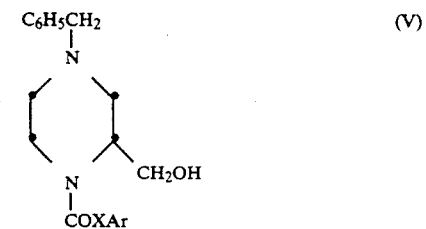

by oxidation using conventional methods, for example, using an oxidising agent such as an acid anhydride or acid chloride complex with dimethylsulphoxide (for example oxalylchloride-dimethylsulphoxide) in a solvent such as dichloromethane followed by treatment with a base such as triethylamine.

Compounds of formula (V) may themselves be prepared from compound (VI)

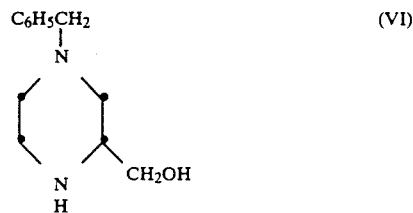

by acylation to introduce the —COXAr moiety according to the method described above. The starting material compound (VI) is a known compound (see, for example European Patent Specification No. 68544).

The intermediates piperazines of formula (II) and (III) are novel compounds and form a further aspect of the invention.

According to another general process (B) compounds of formula (I) may be prepared by reacting a compound of formula (VII)

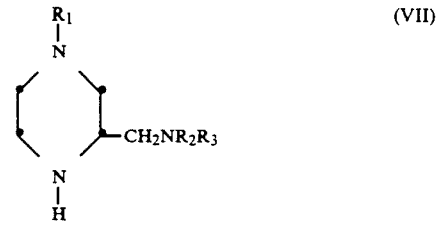

with a reagent serving to introduce the group —COXAr.

For example a compound of formula (VII) may be reacted with an acid $ArXCO_2H$ or an acylating agent corresponding thereto or a salt thereof.

Acylating agents corresponding to the acid $ArXCO_2H$ which may be employed in process (B) include acid halides, for example acid chlorides, alkyl esters and mixed anhydrides as described previously for process (A).

The acylation reaction with an acid $ArXCO_2H$ or an acylating agent corresponding thereto may be effected using similar reaction conditions to those described above for process (A).

Compounds of formula (VII) may be prepared from known compounds by conventional methods. For example, compounds of formula (VII) may be prepared from compounds of formula (VIII)

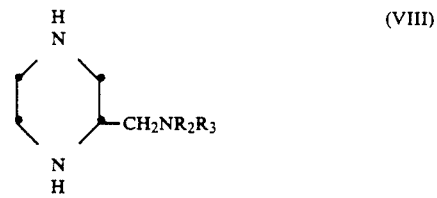

by a selective acylation at the piperazine 4-position using an appropriate acylating agent such as acetic anhydride in a polar solvent such as water. Compounds of formula (VIII) may in turn be prepared by hydrogenation of a compound of formula (IX) using conventional methods.

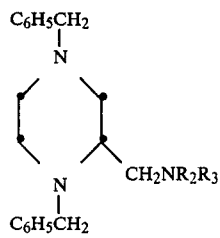

(IX)

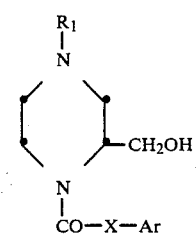

(XII)

Compounds of formula (IX) may be prepared, for example, from compound (X)

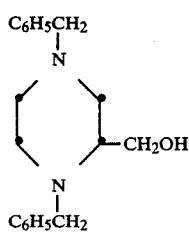

(X)

by oxidation followed by reductive amination according to the method of process (C) below. The oxidation is performed using conventional methods, for example using an oxidising agent such as an acid chloride complex with dimethylsulphoxide in a solvent such as dichloromethane followed by treatment with a base such as triethylamine.

According to a further general process (C), compounds of formula (I) may be prepared by reductive amination of a compound of formula (XI)

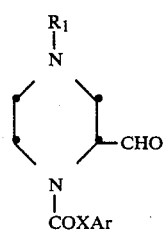

(XI)

with an amine $R_3R_2NH$ in the presence of a suitable reducing agent.

The reduction may be effected using an alkali metal or alkaline earth metal borohydride or cyanoborohydride (for example sodium borohydride or cyanoborohydride) in a suitable solvent, for example an alcohol such as methanol and at a suitable temperature, conveniently room temperature. The reaction may optionally be performed in the presence of an acid such as acetic acid.

Alternatively, the reduction may be effected catalytically, for example, using hydrogen in the presence of a metal catalyst such as Raney nickel, platinum, platinum oxide, palladium or rhodium which may be supported, for example, on charcoal. The reaction may conveniently be carried out in a suitable solvent such as an alcohol (for example ethanol), an amide (for example dimethylformamide) an ether (for example tetrahydrofuran) at a suitable temperature such as ambient temperature and optionally in the presence of an acid catalyst.

Compounds of formula (XI) may be prepared, for example, from compounds of formula (XII)

by oxidation using conventional methods as described above.

Compounds of formula (XII) may themselves be prepared from the corresponding compound of formula (XII)

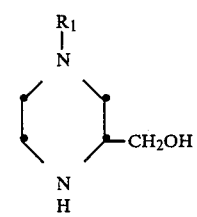

(XII)

by methods analogous to those described for general process (B) above.

The general processes described above may yield the product of the general formula (I) as an individual stereoisomer or as a mixture of stereoisomers. Diastereoisomers may be separated at any convenient point in the overall synthesis by conventional methods, for example chromatography. Specific enantiomers may be obtained by resolution of a racemic mixture at any convenient point in the overall synthesis by the use of conventional methods, see for example "Stereochemistry of Carbon Compounds by E. L. Eliel" (McGraw Hill, 1962).

Where it is desired to isolate a compound of the invention as a salt, this may be formed by conventional methods, for example by treatment with an acid or base in a suitable solvent such as an ether (for example diethyl ether), a nitrile (for example acetonitrile), a ketone (for example acetone) a halogenated hydrocarbon (for example dichloromethane) or an ester (for example ethyl acetate). Salts may also be formed by conversion of one salt into another using conventional methods.

Thus the product of any of process (A) to (C) above may be subjected to one or two further reactions comprising
 (i) converting a compound of formula (I) or a salt thereof into a physiologically acceptable salt thereof.
 (ii) resolution of a racemic mixture to give a specific enantiomer.

The invention is further illustrated by the following non-limiting examples.

All temperatures are in ° C. Chromatography was carried out in the conventional manner using silica gel (Merck, 7729) or by flash column chromatography on silica (Merck 9385) and thin layer chromatography (t.l.c.) on silica except where otherwise stated. Dried refers to drying with $Na_2SO_4$ unless otherwise indicated.

Intermediate 1

1-[(3,4-Dichlorophenyl)acetyl]-2-(1-pyrrolidinylmethyl)piperazine maleate (1:1)

(I)

1-[(3,4-Dichlorophenyl)acetyl]-4-(phenylmethyl)-2-piperazinemethanol 1,1'-Carbonyldiimidazole (236 mg) was added to a stirred solution of 3,4-dichlorophenylacetic acid (314 mg) in dry dichloromethane (6 ml) at room temperature under nitrogen. The resulting solution was stirred at room temperature for 1 h and added dropwise to a cooled solution of 4-(phenylmethyl)-2-piperazinemethanol (300 mg) in dry dichloromethane (3 ml) and stirred at room temperature for 19 h. The reaction mixture was diluted with dichloromethane (5 ml) and washed with 2N sodium carbonate solution (3 × 10 ml). The organic layer was dried and evaporated to give an oil which was purified by flash column chromatography eluting with dichloromethane:ethyl acetate (2:1) to dichloromethane:ethyl acetate (1:1) to dichloromethane:methanol (9:1) to give the title compound as a solid (200 mg). m.p. 148°–150° C.

(II)

1-[(3,4-Dichlorophenyl)acetyl]-4-(phenylmethyl)-2-piperazine carboxaldehyde

A solution of dimethylsulphoxide (369 mg) in dry dichloromethane (3 ml) was added to a stirred solution of oxalyl chloride (300 mg) in dry dichloromethane (7 ml) at −60° under nitrogen and the resulting solution was stirred at −60° to −64° for 30 minutes. The product of stage (1) (774 mg) in dry dichloromethane (5 ml) was added dropwise and the reaction mixture was stirred between −60° to −63° for 2.5 h. Triethylamine (995 mg) was added and the mixture was allowed to warm to −20°, and quenched with water (15 ml). The layers were separated and the aqueous phase was further extracted with dichloromethane (2 × 15 ml). The combined organic extracts were dried and evaporated to give the title compound as an oil (830 mg).

T.l.c. (SiO$_2$) methanol-ethylacetate (3:97) Rf 0.58.

(III)

1-[(3,4-Dichlorophenyl)acetyl]-4-(phenylmethyl)-2-(1-pyrrolidinylmethyl)piperazine maleate A solution of the product of stage (II) (825 mg) in methanol (10 ml) was added to a stirred suspension of pyrrolidine (180 mg) and 3Å molecular sieves (800 mg) in methanol (5 ml), the pH of the mixture being adjusted to 6.5–7 using methanolic hydrogen chloride solution. The reaction mixture was stirred under nitrogen for 15 min and sodium cyanoborohydride (269 mg) was added portionwise. The resulting suspension was stirred under nitrogen for 17 h, filtered and the filtrate was evaporated to dryness. The residue was partitioned between 2N sodium carbonate (30 ml) and dichloromethane (30 ml) and the aqueous layer was further extracted with dichloromethane (2 × 15 ml). The combined organic extracts were dried and evaporated to give a gum which was purified by flash column chromatography eluting with dichloromethane:methanol:0.880 aqueous ammonia (250:8:1) followed by re-purification on an alumina column (UGII, diameter 2.5 cm); eluting with mixtures of ether:methanol (99:1/98:2) to give the free base of the title compound as an oil (181 mg)

A portion of the free base (84 mg) in ethyl acetate was treated with a solution of maleic acid (24 mg) in ethyl acetate to give the title compound as a solid (72 mg) m.p. 117°–120°.

(IV)

1-[(3,4-Dichlorophenyl)acetyl]-2-(1-pyrrolidinylmethyl)piperazine maleate (1:1)

The free base of the product of stage (III) (697 mg) in a mixture of tetrahydrofuran: water (1:1) (14 ml) and concentrated hydrochloric acid (1.4 ml) was hydrogenated over 10% palladium on carbon (50% paste) (560 mg) at atmospheric pressure. The catalyst was filtered off, the filtrate was evaporated and the residue was diluted with water (15 ml) and basified with 2N sodium carbonate solution. The aqueous layer was extracted with dichloromethane (3 × 15 ml) and the combined organic extracts were dried and evaporated to give an oil (526 mg). Purification by flash column chromatography eluting with dichloromethane methanol:0.880 aqueous ammonia (100:8:1) gave the free base of the title compound as an oil (479 mg), a portion of which (60 mg) in ethyl acetate (2 ml) was treated with a solution of maleic acid (39 mg) in ethyl acetate (2 ml). The resulting solid was crystallized from ethyl acetate/methanol to give the title compound as a solid (35 mg) m.p. 160°–162°.

EXAMPLE 1

4-Acetyl-1-[(3,4-dichlorophenyl)acetyl]-2-(1-pyrrolidinylmethyl) piperazine maleate (1:1)

Acetyl chloride (49 mg) was added dropwise to a stirred solution of the free base of Intermediate 1 (200 mg) pyridine (53 mg) and 4-dimethylaminopyridine (5 mg) in dry dichloromethane (5 ml) under nitrogen at 0°. The resulting mixture was allowed to warm to room temperature and stirring was continued for 2 h. The reaction mixture was washed with 2N sodium carbonate solution (2 × 5 ml), dried and evaporated to give an oil which was purified by flash column chromatography on silica gel (M & B, Sorbsil C60 diameter 3.0 cm): eluting with dichloromethane:methanol:0.880 ammonia (200:8:1) to give the free base of the title compound as a colourless gum (190 mg). A portion of free base (160 mg) in ethyl acetate (1 ml) was treated with a solution of maleic acid (51 mg) in ethyl acetate (3 ml). The resulting oil was triturated under dry diethyl ether (3 × 10 ml) to give a solid which was crystallized from ethyl acetate/methanol to give the title compound as a solid (97 mg) m.p. 137°–140°.

Analysis. Found: C,53.73; H,5.65; N,8.12. $C_{19}H_{25}Cl_2N_3O_2$. $C_4H_4O_4$ requires C,53.70; H,5.68; N,8.17%.

EXAMPLE 2

1-[(3,4-Dichlorophenyl)acetyl]-4-(1-oxobutyl)-2-(1-pyrrolidinylmethyl) piperazine maleate (1:1)

Following the method of Example 1, butyryl chloride (49 mg) was reacted with the free base of Intermediate 1 (150 mg) to give the title compound as a solid (133 mg) following purification by flash column chromatography eluting with dichloromethane:methanol:0.880 ammonia (250:8:1) and maleate salt formation; m.p. 172°–174°.

Analysis. Found: C,55.49; H,6.28; N,7.68. $C_{21}H_{29}Cl_2N_3O_2$. $C_4H_4O_4$ requires C,55.35; H,6.13; N,7.75%.

EXAMPLE 3

Methyl 4-[(3,4-dichlorophenyl)acetyl]-α-oxo-3-(1-pyrrolidinyl-methyl)-1-piperazineacetate maleate (1:1)

Following the method of Example 1 and using equivalent quantities of the appropriate starting materials the title compound was prepared as a solid (169 mg) after purification by flash column chromatography eluting with dichloromethane:methanol:ammonia (250:8:1) and maleate salt formation, m.p. 185°–188°.

Analysis. Found: C,51.31; H,5.20; N,7.24. $C_{20}H_{25}Cl_2N_3O_4 \cdot C_4H_4O_4$ requires C,51.62; H,5.23; N,7.52%.

EXAMPLE 4

1-[(3,4-Dichlorophenyl)acetyl]-4-(1-oxo-2-propenyl)-2-(1-pyrrolidinyl methyl)piperazine fumarate (1:1)

Acryloyl chloride (56 mg) was added to a stirred solution of Intermediate 1 (200 mg), pyridine (53 mg) and 4-dimethylaminopyridine (5 mg) in dry dichloromethane (5 ml) under nitrogen at 0°. The resulting solution was allowed to warm to room temperature and stirring was continued for 1 h. The reaction mixture was washed with aqueous 2N sodium carbonate solution (2×5 ml), the organic phase was dried and evaporated to give an oil which was purified by flash column chromatography on silica gel eluting with dichloromethane:methanol:0.880 $NH_3$ (250:8:1) to give the free base of the title compound as a foam (157 mg). A solution of the free base (142 mg) in ethyl acetate was treated with a solution of fumaric acid (44 mg) in ethyl acetate/methanol. The resulting solid was crystallized from ethyl acetate/methanol to give the title compound as a solid (106 mg) m.p. 163°–166°.

Analysis. Found: C,54.46; H,5.54; N,7.83. $C_{20}H_{25}Cl_2N_3O_2 \cdot C_4H_4O_4$ requires C,54.76; H,5.55; N,7.98%.

EXAMPLE 5

1-[(3,4-Dichlorophenyl)acetyl]-4-(formyl)-2-(1-pyrrolidinylmethyl) piperazine fumarate (1:1)

A mixture of Intermediate 1 (200 mg) and methyl formate (3 ml) was allowed to stand at room temperature for 18 h. The excess methyl formate was removed in vacuo and the residue was purified by flash column chromatography on silica gel eluting with dichloromethane:methanol:0.880 ammonia (100:8:1) to give the free base of the title compound as an oil (164 mg). A portion of the free base (150 mg) was further treated as described in Example 4 to give the title compound as a solid (122 mg) m.p. 179°–182°.

Analysis. Found:C,52.93; H,5.49; N,8.30. $C_{18}H_{23}Cl_2N_3O_2 \cdot C_4H_4O_4$ requires C,52.81; H,5.44; N,8.40%.

EXAMPLE 6

1-[(3,4-Dichlorophenyl)acetyl]-4-(1-oxopropyl)-2-(1-pyrrolidinyl methyl)piperazine 1,1'-Carbonyldiimidazole (100 mg) was added to a stirred solution of propionic acid (47 mg) in dry dichloromethane (3 ml) at room temperature under nitrogen and the resulting solution was stirred at room temperature for 1 h. A solution of Intermediate 1 (200 mg) in dry dichloromethane (3 ml) was added and stirring was continued for a further 20 h. The reaction mixture was diluted with dichloromethane (5 ml) and washed with aqueous 2N sodium carbonate solution (2×5 ml). The organic layer was dried and evaporated to give an oil, which solidified. The solid was triturated under dry diethyl ether and the resulting solid was crystallized from t-butylmethyl ether to give the title compound as a solid (90 mg) m.p. 110°–112°.

Analysis. Found: C,58.34; H,6.71; N,10.28. $C_{20}H_{27}Cl_2N_3O_2$ requires C,58.25; H,6.60; N,10.19%.

EXAMPLE 7

4-Acetyl-1[(4-chlorophenoxyacetyl]-2-(1-pyrrolidinyl-methyl)piperazine fumarate (1:1)

(i)

1,4-Bis(phenylmethyl)-2-(1-pyrrolidinylmethyl)piperazine

A solution of oxalylchloride (1.4 ml) in dry dichloromethane (30 ml) at −60° was treated with a solution of dry dimethylsulphoxide (1.7 ml) in dry dichloromethane (10 ml) over a 10 min period. The mixture was stirred at −60° for 20 min, a solution of 1,4-bis(phenylmethyl)-2-piperazine methanol (2.7 g) in dry dichloromethane (20 ml) was added over 15 min and the mixture was stirred at −60° to −65° for 3 h. Triethylamine (4.7 ml) was added followed by water (60 ml) at −30°. The product was extracted with dichloromethane (30 ml), dried, filtered and evaporated to give an oily residue.

A solution of the oil and pyrrolidine (0.91 ml) in methanol (50 ml) at −50° was treated with methanolic hydrogen chloride (pH 6.5). The mixture was allowed to warm up to ambient temperature and 3Å Molecular Sieves (4.0 g), and sodium cyanoborohydride (1.1 g) were added. The mixture was stirred at ambient temperature for 18 h, filtered and the filtrate was evaporated in vacuo. The residue was dissolved in dichloromethane (75 ml) and washed with aqueous sodium carbonate solution (1M; 50 ml). The organic solution was dried and evaporated to give a residue (3.2 g) which was purified by flash column chromatography eluting with dichloromethane/methanol/ammonia (200:8:1) to give the title compound as an oil (2.06 g).

T.l.c. $SiO_2$ dichloromethane/methanol/ammonia (150:8:1) Rf 0.2.

(ii) 2-(1-Pyrrolidinylmethyl)piperazine

A solution of the product of stage (i) (1.75 g) in a mixture of tetrahydrofuran (20 ml), water (20 ml) and conc hydrochloric acid (4.35 ml) was hydrogenated over 10% palladium on carbon (0.5 g) until uptake of hydrogen ceased. The reaction mixture was filtered and the filtrate was evaporated in vacuo. The solid residue was triturated under boiling methanol (20 ml) to give the title compound as a solid (1.15 g). m.p. 290° decomp.

T.l.c. $SiO_2$/dichloromethane/methanol/ammonia (75:10:2), Rf 0.05.

(iii) 1-Acetyl-3-(1-pyrrolidinylmethyl)piperazine

A solution of the product of stage (ii) (1 g) in a mixture of water (10 ml) and triethylamine (2.5 ml) was treated with a solution of acetic anhydride (0.34 ml) in water (10 ml) over 30 min. The mixture was stirred at ambient temperature for 2 h. An additional quantity of acetic anhydride (0.28 ml) in water (5 ml) was added over a 10 min period. Sodium chloride (6 g) and sodium carbonate (3 g) were added and the product was extracted with dichloromethane (5×50 ml). The combined organic extracts were dried and evaporated. The residue (0.8 g) was purified by flash column chromatography eluting with dichloromethane/methanol/ammonia (150:8:1) to give the title compound as an oil (0.677 g).

T.l.c. SiO$_2$/Dichloromethane/methanol/ammonia (75:10:2) Rf 0.3.

(iv) 4-Acetyl-1-[(4-chlorophenoxy)acetyl]-2-(1-pyrrolidinylmethyl) piperazine fumarate (1:1)

A mixture of p-chlorophenoxyacetic acid (0.2 g) and 1,1'-carbonyldiimidazole (0.173 g) in dry dichloromethane (5 ml) was stirred at ambient temperature for 40 min. A solution of the product of stage (iii) (0.15 g) in dry dichloromethane (5 ml) was added and the mixture was stirred at ambient temperature for 18 h. The reaction mixture was poured into aqueous sodium carbonate solution (2N, 100 ml) and extracted with dichloromethane (50 ml). The organic solution was dried, and evaporated in vacuo and the residue was purified by flash column chromatography eluting with dichloromethane/methanol/ammonia (200:8:1) to give the free base of the title compound as a foam (0.24 g). A solution of the base in ethyl acetate (5 ml) was treated with a solution of fumaric acid (80 mg) in methanol (2 ml). The solid was crystallized from a mixture of ethyl acetate and methanol to give the title compound as a solid (0.104 g) m.p. 160°-2°.

Assay. Found: C, 54.18; H, 5.98; N, 7.54. $C_{19}H_{26}ClN_3O_3.1\tfrac{1}{2}C_4H_4O_4$ requires C, 54.20; H, 5.82; N, 7.58%.

EXAMPLE 8

Following the method of Example 7 (iv) and using equivalent quantities of the appropriate starting materials there were prepared (a) 4-Acetyl-2-(1-pyrrolidinylmethyl)-1-[[4-(trifluoromethyl)phenyl]acetyl]piperazine fumarate (1:1) as a solid (0.26 g) m.p. 120°-1°.

Assay. Found: C, 55.76; H, 5.85; N, 8.03. $C_{20}H_{26}F_3N_3O_2.C_4H_4O_4$ requires C, 56.14; H, 5.81; N, 8.18%.

(b) 4-Acetyl-1-(1-naphthalenylacetyl)-2-(1-pyrrolidinylmethyl) piperazine fumarate (1:1) as a solid (0.162 g) m.p. 185°-7°.

Assay. Found: C, 65.37; H, 6.80; N, 8.37. $C_{23}H_{29}N_3O_2.C_4H_4O_4$ requires C, 65.44; H, 6.71; N, 8.48%.

EXAMPLE 9

4-Acetyl-1-[(3,4-dichlorophenyl)acetyl]-2-(1,2,3,6-tetrahydro-1-pyridinylmethyl)piperazine fumarate (2:1)

(i) 4-Acetyl-2-piperazinemethanol

A solution of 2-piperazinemethanol (197 mg) and triethylamine (0.35 ml, 0.26 g) in water (4 ml) was treated with a mixture of acetic anhydride (0.16 ml) and water (1.5 ml) and was stirred at room temperature for 2 h. The solution was basified with sodium carbonate solution (2N, 1 ml), saturated with sodium chloride (1 g) and washed with dichloromethane (10 ml). The aqueous phase was evaporated in vacuo to give a solid which was purified by flash column chromatography eluting with dichloromethane:methanol:ammonia, (75:10:1.5) to give the title compound as an oil (188 mg).

T.l.c. SiO$_2$ dichloromethane/methanol/ammonia 75:10:2) Rf 0.23.

(ii) 4-Acetyl-1-[(3,4-dichlorophenyl)acetyl]-2-piperazinemethanol

To a solution of 1,1'Carbonyldiimidazole (3.86 g) in dry dichloromethane (150 ml) was added 3,4-dichlorophenylacetic acid (4.86 g) and the resulting solution was stirred under nitrogen for 0.5 h at room temperature. A solution of the product of stage (i) (1.51 g) in dichloromethane (50 ml) was added and the mixture was stirred at room temperature, for 18 h. The reaction mixture was washed with sodium carbonate solution (2N, 2×100 ml) and hydrochloric acid (0.5N, 100 ml). The organic solution was dried (Na$_2$SO$_4$ and MgSO$_4$), filtered and evaporated to give a solid (18 g). The solid was extracted with dichloromethane (2×50 ml) and the extracts evaporated to give a solid (5.1 g). A solution of the solid in a mixture of tetrahydrofuran (60 ml) and water (20 ml) was treated with lithium hydroxide (403 mg) and the mixture was stirred at room temperature for 0.25 h. A further portion of lithium hydroxide (403 mg, 9.6 mmol) was added and the mixture was stirred for 0.25 h. The organic solvent was evaporated in vacuo and dichloromethane (150 ml) was added to the aqueous residue. The mixture was filtered, the filtrate layers separated and the organic extract was dried and evaporated in vacuo to give a foam (2.37 g). The foam was purified by flash column chromatography eluting with dichloromethane:methanol:ammonia (75:10:2) to give the title compound as a gum (2.2 g).

T.l.c. SiO$_2$ /Dichloromethane/methanol/ammonia (75:10:2) Rf 0.28.

(iii) 4-Acetyl-1-[(3,4-dichlorophenyl)acetyl]-2-piperazinecarboxaldehyde

A solution of dimethylsulphoxide (0.52 ml) in dry dichloromethane (6 ml) was added to a stirred solution of oxalyl chloride (0.40 ml) in dry dichloromethane (30 ml), at −65° under nitrogen. The resulting solution was stirred at −55° for 30 min and a solution of the product of stage (ii), (1.04 g) in dry dichloromethane (25 ml) was added dropwise at −65°. The reaction mixture was stirred at −65° for 3 h. Triethylamine (2.5 ml) was added, followed by water (25 ml) at −20°. The layers were separated and the aqueous solution was extracted with dichloromethane (2×30 ml). The combined organic extracts were dried and evaporated to give the title compound as a gum (1.4 g).

T.l.c. SiO$_2$, Ethyl acetate/methanol (10:1) Rf 0.32.

(iv) 4-Acetyl-1-[(3,4-dichlorophenyl)acetyl]-2-(1,2,3,6-tetrahydro-1-pyridinylmethyl)piperazine fumarate (2:1)

A solution of the product of stage (iii) (517 mg) in dry methanol (15 ml) was added to a stirred suspension of tetrahydropyridine (0.2 ml) and 3Å molecular sieves (1 g) in dry methanol (10 ml). The pH of the reaction mixture was adjusted to 6 using methanolic hydrogen chloride solution, sodium cyanoborohydride (200 mg) was added and the resulting mixture was stirred for 18 h. The mixture was filtered and the filtrate evaporated. The residue was dissolved in 2N sodium carbonate solution (10 ml) and extracted with dichloromethane (3×10 ml). The dichloro-methane extracts were evaporated to dryness, the residue was extracted with hydrochloric acid (0.1M, 4.5 mmol) and washed with ether (3×10 ml). The aqueous solution was basified with sodium carbonate solution (2N, 10 ml) and the product was extracted into dichloromethane (3×10 ml). The combined extracts were dried and evaporated to give a gum (550 mg), which was purified by flash column chromatography eluting with dichloromethane:methanol:0.88 ammonia (75:8:1) to give the free base of the title compound as a white foam (250 mg). The foam (225 mg) was dissolved in ethyl acetate (10 ml) and treated with a hot solution of fumaric acid (67 mg) in methanol (1 ml) to give the title compound as a solid (172 mg) m.p. 109°–112°.

Analysis. Found: C, 53.8; H, 6.0; N, 7.5. $C_{20}H_{25}N_3Cl_2O_2 \cdot MeOH \cdot 0.83 C_4H_4O_4 \cdot 0.45 H_2O$ requires C, 53.4; H, 6.1; N, 7.7%.

EXAMPLE 10

4-Acetyl-1-[(3,4-dichlorophenyl)acetyl]-2-[(dimethylamino)methyl]piperazine hydrochloride Following the method of Example 9(IV) and using equivalent quantities of the appropriate starting materials the free base of the title compound was prepared as a gum (143 mg) after purification by column chromatography on activity III alumina eluting with ethyl acetate:methanol (40:1). The gum was dissolved in ether (5 ml) and treated with ethereal hydrogen chloride (2 ml). The mixture was evaporated in vacuo and the residue crystallized from ethyl acetate:methanol (~5:1, 10 ml) to give the title compound as a solid (34 mg) m.p. 264°–268° (softens at 64°).

Analysis. Found: C, 50.1; H, 6.0; N, 10.2. $C_{17}H_{23}N_3Cl_2O_2 \cdot HCl$ requires C, 49.95; H, 5.9; N, 10.3%.

EXAMPLE 11

Methyl 4-[(3,4-dichlorophenyl)acetyl]-3-(1-pyrrolidinylmethyl)-1-piperazinecarboxylate fumarate (1:1)

Methylchloroformate (39 mg) was added to a stirred solution of the free base of Intermediate 1 (139 mg) and triethylamine (45 mg) in dry dichloromethane (3 ml) at 0° under nitrogen. The resulting solution was allowed to warm to room temperature and stirring was continued for 1 h. A further quantity of methyl chloroformate (22 mg) was added and stirring continued for a further 30 min. The reaction mixture was washed with aqueous 2N sodium carbonate solution (5 ml) and the aqueous layer was further extracted with dichloromethane (2×5 ml). The combined organic extracts were dried and evaporated to give a foam which was purified by flash column chromatography on silica gel eluting with dichloromethane:methanol:0.880 NH₃ (200:8:1) to give the free base of the title compound as an oil. A solution of the free base (87 mg) in ethyl acetate was treated with a solution of fumaric acid (27 mg) in ethyl acetate. The resulting solid was crystallized from ethyl acetate/methanol to give the title compound as a solid (84 mg) m.p. 178°–180°.

Assay. Found C, 52.12; H, 5.66; N, 7.81. $C_{19}H_{25}Cl_2N_3O_3 \cdot C_4H_4O_4$ requires C, 52.08; H, 5.51; N, 7.92%.

EXAMPLE 12

Ethyl 4-[(3,4-dichlorophenyl)acetyl]-3-(1-pyrrolidinylmethyl)-1-piperazinecarboxylate fumarate (1:1)

Ethylchloroformate (72 mg) was added to a stirred solution of the free base of Intermediate 1 (200 mg) and triethylamine (65 mg) in dry dichloromethane (4 ml) at 0° under nitrogen. The resulting solution was allowed to warm to room temperature and stirring was continued for 2.5 h. The reaction mixture was washed with aqueous 2N sodium carbonate solution (5 ml). The aqueous layer was further extracted with dichloromethane (2×5 ml), the combined organic extracts were dried and evaporated to give an oil. The oil was purified by flash column chromatography on silica gel eluting with dichloromethane:methanol:0.880 NH₃ (250:8:1) to give the free base of the title compound as an oil (80 mg), a solution of which in ethyl acetate was treated with a solution of fumaric acid (24 mg) in ethyl acetate/methanol. The resulting solid was filtered off and crystallized from ethyl acetate/methanol to give the title compound as a solid (55 mg) m.p. 190°–192°.

Assay. Found C, 52.68; H, 5.66; N, 7.46. $C_{20}H_{27}Cl_2N_3O_3 \cdot C_4H_4O_4$ requires C, 52.95; H, 5.74; N, 7.72%.

EXAMPLE 13

Propyl 4-[(3,4-dichlorophenyl)acetyl]-3-(1-pyrrolidinylmethyl)-1-piperazinecarboxylate fumarate (1:1)

A mixture of the free base of Intermediate 1 (0.2 g) and dry triethylamine (0.082 ml) in dry dichloromethane (5 ml) at −20° was treated with a solution of n-propyl chloroformate (0.065 ml) in dry dichloromethane (2 ml) dropwise over a 5 minute period. The reaction mixture was stirred at −20° for 20 minutes and then was treated with an aqueous solution of sodium carbonate (1M; 15 ml). The product was extracted with dichloromethane (2×20 ml). The organic extract was dried and evaporated in vacuo. The residue was purified by flash column chromatography eluting with dichloromethane:methanol:0.88 NH₃ 200:8:1 to give the free base of the title compound as an oil (0.22 g). A solution of the free base (0.22 g) in ethyl acetate (5 ml) was treated with a solution of fumaric acid (70 mg) in a mixture of ethyl acetate and methanol. The solid was crystallised from a mixture of ethyl acetate and methanol to give the title compound as a solid (0.165 g) m.p. 187°.

Assay. Found: C, 53.53; H, 5.87; N, 7.32. $C_{21}H_{29}Cl_2N_3O_3 \cdot C_4H_4O_4$ requires C, 53.77; H, 5.96; N, 7.58%.

EXAMPLE 14

Methyl 4-[(3,4-dichlorophenyl)acetyl]-3-(1,2,3,6-tetrahydro-1-pyridinylmethyl)-1-piperazinecarboxylate fumarate (1:1)

(i) Methyl-3-(hydroxymethyl)-1-piperazine carboxylate

A solution of 2-piperazinemethanol (432 mg) and dry triethylamine (0.7 ml) in dry acetonitrile (40 ml) at 5° was treated with a solution of methyl chloroformate (0.29 ml) in dry acetonitrile (5 ml) dropwise over 0.5 min. The reaction mixture was stirred for 10 min and an aqueous solution of sodium carbonate (2N, 20 ml) was added. The mixture was evaporated, sodium carbonate solution (10 ml) added and the mixture was extracted with dichloromethane (3×10 ml). The aqueous phase was saturated with sodium chloride, and further extracted with dichloromethane (3×10 ml). The combined organic solutions were dried, filtered and evaporated in vacuo to give an oily residue (0.5 g) which was purified by flash column chromatography eluting with dichloromethane:methanol:ammonia (100:10:2) to give the title compound as an oil (147 mg).

T.l.c. SiO$_2$ Dichloromethane:methanol:aq ammonia (100:10:2) Rf. 0.13.

T.l.c. SiO$_2$ Dichloromethane:methanol:aq ammonia (25:10:1) Rf. 0.59.

(ii) Methyl 4-[(3,4-dichlorophenyl)acetyl]-3-(hydroxymethyl)-1-piperazinecarboxylate To a solution of 1,1'-carbonyldiimidazole (3.26 g) in dry dichloromethane (120 ml) was added portionwise 3,4-dichlorophenylacetic acid (4.12 g) and the resulting solution stirred under nitrogen for 1 h, at room temperature. A solution of the product of stage (i) (1.4 g) in dichloromethane (120 ml) was added and the mixture stirred at room temperature for 18 h. The reaction mixture was washed with sodium carbonate solution (2N, 2×100 ml), dried and evaporated to give a gum (5.36 g), a solution of which in a mixture of tetrahydrofuran (80 ml) and water (25 ml) was treated with lithium hydroxide (671 mg) and the mixture was stirred at room temperature for 0.5 h. The organic solvent was evaporated in vacuo and the aqueous residue was extracted with dichloromethane (3×50 ml). The organic extracts were dried and evaporated in vacuo to give a gum which was purified by flash column chromatography eluting with ethyl acetate:methanol (40:1) to give the title compound as a foam (2.2 g).

T.l.c. SiO$_2$ Dichloromethane:methanol:aq ammonia 150:8:1 Rf 0.32.

(iii) Methyl 4-[(3,4-dichlorophenyl)acetyl]-3-formyl-1-piperazinecarboxylate A solution of dimethylsulphoxide (0.52 ml) in dry dichloromethane (6 ml) was added to a stirred solution of oxalyl chloride (0.40 ml) in dry dichloromethane (30 ml) at −65° under nitrogen. The resulting solution was stirred at −65° for 20 min and a solution of the product of stage (ii) (1.08 g) in dry dichloromethane (25 ml) was added dropwise at −65°. The reaction mixture was stirred at −65° for 3 h. Triethylamine (2.5 ml) was added, followed by water (25 ml) at −20°. The layers were dried and evaporated to give the title compound as a gum (1.5 g).

T.l.c. SiO$_2$ Ethylacetate:methanol (19:1) Rf 0.5.

(iv) Following the method of Example 9(iv), the title compound was prepared as a powder (180 mg) from the product of stage (iii) (539 mg) after purification by flash column chromatography eluting with dichloromethane:methanol:aq ammonia (300:8:1) and fumarate salt formation m.p. 158°–160°.

Analysis. Found: C, 53.0; H, 5.0; N, 7.45. C$_{20}$H$_{25}$N$_3$Cl$_2$O$_3$·C$_4$H$_4$O$_4$ requires C, 53.1; H, 5.4; N, 7.75%.

EXAMPLE 15

Methyl 4-[(3,4-dichlorophenyl)acetyl]-3-[(dimethylamino)methyl]-1-piperazinecarboxylate monohydrochloride Following the method of Example 9(iv) and using equivalent quantities of the appropriate starting materials the title compound was prepared as crystals (116 mg) after purification by column chromatography on activity III alumina eluting with ethyl acetate:methanol and hydrochloride formation, m.p. 229°–231°.

Analysis. Found: C, 48.1; H, 5.8; N, 9.9. C$_{17}$H$_{23}$N$_3$Cl$_2$O$_3$·HCl requires C, 48.05; H, 5,5; N, 9.9%.

EXAMPLE 16

Methyl-4-[(4-chlorophenyl)acetyl]-3-(1-pyrrolidinylmethyl)-1-piperazinecarboxylate fumarate (1:1)

(i) Methyl 4-[(4-chlorophenyl)acetyl]-3-(hydroxymethyl)-1-piperazinecarboxylate Following the method of Example 14(ii) the title compound was prepared as a foam (606 mg) from methyl-3-(hydroxymethyl)-1-piperazinecarboxylate (603 mg) and p-chlorophenylacetic acid (1.47 g) after purification by flash column chromatography with gradient elution using ethyl acetate and ethyl acetate:methanol (19:1).

T.l.c. SiO$_2$ Ethylacetate, Rf 0.3.

(ii) Methyl-4-[(4-chlorophenyl)acetyl]-3-(1-pyrrolidinylmethyl)-1-piperazinecarboxylate fumarate (1:1)

A solution of dimethylsulphoxide (0.16 ml) in dry dichloromethane (2 ml) was added to a stirred solution of oxalyl chloride (0.12 ml) in dry dichloromethane (10 ml) at −55° under nitrogen. The resulting solution was stirred at −55° for 30 min followed by dropwise addition of a solution of the product of stage (i) (0.30 g) in dry dichloromethane (8 ml) at −55°. The reaction mixture was stirred at −55° for 3 h. Triethylamine (0.78 ml) was added and the mixture was allowed to warm to −20°, and quenched with water (6 ml). The layers were separated and the aqueous layer was further extracted with dichloromethane (2×10 ml). The combined organic extracts were dried and evaporated to give an oil which was dissolved in dry methanol (6 ml) and added to a stirred suspension of pyrrolidine (0.11 ml) and 3Å molecular sieves (0.5 g) in methanol (4 ml). The pH of the reaction mixture was adjusted to 6 using methanolic hydrogen chloride solution, sodium cyanoborohydride (130 mg) was added and the resulting mixture was stirred for 3 days. The mixture was filtered and the filtrate was evaporated to dryness. The mixture was partitioned between 2N sodium carbonate solution (5 ml) and dichloromethane (3×5 ml). The dichloromethane extracts were evaporated to dryness. The residue was acidified with hydrochloric acid (0.1M) and extracted with ether (3×5 ml). The aqueous solution was basified with sodium carbonate (2N, 5 ml) and the product extracted into dichloromethane (3×5 ml). The extracts were dried and evaporated to give a gum (360 mg) which was purified by flash column chromatography eluting with dichloromethane:methanol:ammonia, (150:8:1), to give the product (198 mg). Further purification by column chromatography on activity III alumina eluting with dichloromethane:methanol:ammonia (40:1:0.1) gave the free base of the title compound as a gum (188 mg). The gum was dissolved in ethyl acetate (10 ml) and treated with a hot solution of fumaric acid (64 mg) in methanol (1 ml) to give the fumarate salt which was combined with the product from a previous preparation (80 mg) and crystallised from ethyl acetate:-methanol, 10:1, (10 ml) to give the title compound as a solid (265 mg), mp 147°–149°.

Analysis. Found: C, 55.1; H, 6.05; N, 8.15. $C_{19}H_{26}ClN_3O_3.C_4H_4O_4.O.O6H_2O$ requires C, 55.6; H, 6.1; N, 8.45%. Water analysis. Found: 0.22% $H_2O$ w/w ≈ 0.06 mol %.

The following examples illustrate pharmaceutical formulations containing methyl 4-[(3,4-dichlorophenyl)acetyl]-3-(1-pyrrolidinylmethyl)-1-piperazinecarboxylate. Other compounds of the invention may be formulated in a similar manner.

TABLETS FOR ORAL ADMINISTRATION

DIRECT COMPRESSION

|  | mg/tablet |
|---|---|
| Active ingredient | 20 |
| Calcium Hydrogen Phosphate B.P.* | 75.5 |
| Croscarmellose sodium USP | 4 |
| Magnesium Stearate, B.P. | 0.5 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

INJECTION FOR INTRAVENOUS ADMINISTRATION

|  | mg/ml |
|---|---|
| Active ingredient | 5 |
| Sodium Chloride BP | as required |
| Water For Injection BP 0.5 to 2 ml | |

INTRAVENOUS INFUSION

| Dextrose 5% aqueous solution BP | 10–100 ml |
|---|---|
| Active ingredient | 700 mg |
| Sodium Chloride BP | as required |

For infusion at a rate of 700 mg per hour.

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

EXAMPLE 17

(R)-Methyl 4-[(3,4-dichlorophenyl)acetyl]-3-(1-pyrrolidinylmethyl)-1-piperazinecarboxylate fumarate (1:1)

(i) (R)-3-(Hydroxymethyl)-2,5-piperazinedione

A mixture of glycyl-D-serine I (4 g) in methanol (12 ml) was treated with thionyl chloride (4 ml) dropwise over a 15 min period maintaining the temperature below 30°. The mixture was heated at 40°–50° for 3 h, and the solvent was evaporated in vacuo. The residue was triturated under diethyl ether and then dissolved in methanol (80 ml). Aqueous ammonia (8 ml) was added and the resulting solid was filtered off, to give the title compound as a solid (1.95 g) m.p. 218°.

$[\alpha]_D^{20}$ −58.13° (0.6% w/v DMSO).

(ii) (S)-2-Piperazinemethanol

The product of stage (i) (0.9 g) was gradually added to a refluxing suspension of lithium aluminium hydride (1.5 g; 0.039 mol in dry tetrahydrofuran (250 ml) over 20 h via continuous extraction from a Soxhlet extractor. The mixture was cooled, water (1.5 ml) was cautiously added followed by aqueous sodium hydroxide (2M; 4.5 ml) and water (1.5 ml). The mixture was filtered and the filtrate was evaporated in vacuo. The residue (0.2 g) was crystallized from acetonitrile (5 ml) to give the title compound as a solid (0.04 g) m.p. 123°–6°.

(iii) (S)-Methyl 3-(hydroxymethyl)-1-piperazinecarboxylate

A solution of the product of stage (ii) (0.080 g) in dry acetonitrile (10 ml) was treated with a solution of methyl chloroformate (71 mg; 0.75 mmol) in dry acetonitrile (3 ml) over a 5 min period. The mixture was stirred at ambient temperature for 30 min and aqueous sodium carbonate solution (1 ml) was added. The solvent was removed in vacuo and the aqueous residue was extracted with dichloromethane (3×25 ml) and chloroform (3×25 ml). The extract was washed with aqueous sodium carbonate solution (5 ml: 1M), and the combined extracts were dried and evaporated in vacuo to give the title compound as an oil (0.1 g).

T.l.c. $SiO_2/CH_2Cl_2/CH_3OH/NH_3$ 75:10:2 Rf 0.35.

(iv) (S)-Methyl 4-[(3,4-dichlorophenyl)acetyl]-3-(hydroxymethyl)-1-piperazinecarboxylate A solution of 3,4-dichlorophenylacetic acid (0.35 g) and 1,1-carbonyldiimidazole (0.28 g) in dry dichloromethane (5 ml) was stirred at ambient temperature for 1 h. A solution of the product of stage (ii) (0.1 g) in dry dichloromethane (2 ml) was added and the mixture was stirred at ambient temperature for 20 h. The mixture was diluted with dichloromethane (30 ml) and washed with aqueous sodium carbonate solution (1M; 3×50 ml). The organic solution was dried and evaporated to give an oily residue (0.433 g), a solution of which in a mixture of tetrahydrofuran and water (6 ml; 1:1) was treated with lithium hydroxide (50 mg; 1.2 mmol). The mixture was stirred at ambient temperature for 1 h and the organic solvent was removed in vacuo. The aqueous residue was extracted with dichloromethane (3×50 ml), dried and evaporated to give an oily residue (0.2 g) which was purified by flash column chromatography eluting with ethyl acetate/methanol 40:1 to give the title compound as a gum (0.185 g).

T.l.c. (SiO$_2$/dichloromethane/methanol/ammonia 150:8:1) Rf 0.3.

(v) (R)-Methyl 4-[(3,4-dichlorophenyl)acetyl]-3-(1-pyrrolidinylmethyl)-1-piperazinecarboxylate fumarate (1:1)

A solution of oxalyl chloride (0.1 ml) in dry dichloromethane (3 ml) at −70° was treated with a solution of dry dimethylsulphoxide (0.21 ml) in dry dichloromethane (2 ml) over a 5 min period. The mixture was stirred at −70° for 10 min and a solution of the product of stage (iv) (0.18 g) in dry dichloromethane (3 ml) was added. The reaction mixture was stirred at −70° for 140 min and a solution of N-methylmorpholine (0.25 ml) in dry dichloromethane (2 ml) was added. The mixture was stirred at −20° to −15° for 35 min and hydrochloric acid (0.01M; 20 ml) was added. The product was extracted with dichloromethane (2×10 ml), the combined extracts were washed with hydrochloric acid (0.01M; 10 ml), dried and evaporated to give an oily residue (0.1 g). A solution of pyrrolidine hydrochloride (0.1 g) in methanol (3 ml) at 0° was treated with 3Å molecular sieves (0.1 g) followed by a solution of the above residue in methanol (2 ml). The mixture was stirred for 5 min and sodium cyanoborohydride (60 mg) was added. The mixture was stirred at ambient temperature for 2 days and then filtered through cotton wool. The filtrate was evaporated in vacuo and the residue was dissolved in dichloromethane (50 ml). The solution was washed with aqueous sodium carbonate (1M; 20 ml) dried and evaporated to give an oily residue which was purified by flash column chromatography eluting with dichloromethane/methanol/ammonia (200:8:1). A solution of the residue in ethyl acetate (2 ml) was treated with a solution of fumaric acid (8 mg) in a mixture of ethyl acetate and methanol (2 ml). The resulting solid was crystallized from a mixture of ethyl acetate and methanol to give the title compound as a solid (0.020 g), m.p. 184°–185°.

Analysis. Found: C, 51.70; H, 5.75; N, 7.72. $C_{19}H_{25}Cl_2N_3O_3 \cdot C_4H_4O_4$ requires C, 52.08; H, 5.51; N, 7.92%.

We claim:

1. A compound of formula (I)

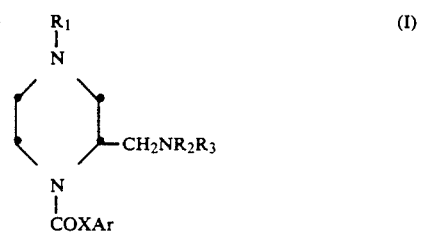

wherein
R$_1$ represents —COR$_4$, —CO$_2$R$_4$ or —COCO$_2$R$_4$ (where R$_4$ represents a hydrogen atom or a C$_{1-6}$ alkyl or c$_{2-6}$ alkenyl group;
R$_2$ and R$_3$ are the same or different and are C$_{1-6}$ alkyl or C$_{3-6}$ alkenyl; or —NR$_2$R$_3$ forms a 5-membered (optionally containing an oxygen atom adjacent to the nitrogen) or 6-membered ring, which ring optionally contains one unit of unsaturation and which is unsubstituted or substituted by methylidene optionally substituted by a group selected from nitrile, phenyl, carboxyl, amido, C$_{1-6}$ alkyl, phen(C$_{1-6}$)alkyl, C$_{1-6}$ hydroxyalkyl, C$_{1-6}$ carboxyalkyl and C$_{1-6}$ amidoalkyl, —COR$_5$ (where R$_5$ represents C$_{1-6}$ alkyl, —OR$_6$ or —NHR$_6$ and R$_6$ represents hydrogen, C$_{1-6}$ alkyl, phenyl, or phen(C$_{1-6}$)alkyl or =NOR$_7$ (where R$_7$ represents C$_{1-6}$ alkyl);
X represents a direct bond, —CH$_2$—or —CH$_2$O—;
Ar represents a phenyl moiety substituted by one or more groups or atoms selected from halogen atoms, C$_{1-6}$ alkyl, —CF$_3$ and NO$_2$ groups, or by two substituents which form a second ring; or a physiologically acceptable salt thereof.
2. A compound according to claim 1 wherein R$_1$ represents —COR$_4$.
3. A compound according to claim 1 wherein R$_1$ represents —CO$_2$R$_4$.
4. A compound according to claim 1 wherein —NR$_2$R$_3$ represents a pyrrolidine ring.
5. A compound according to claim 1 wherein X represents —CH$_2$— and Ar represents halosubstituted phenyl.
6. A compound according to claim 1 wherein R$_4$ represents —CH$_3$, —CH$_2$CH$_3$, —CH=CH$_2$, —OCH$_3$ or —OCH$_2$CH$_3$.
7. A compound selected from
4-Acetyl-1-[(3,4-dichlorophenyl)acetyl]-2-(1-pyrrolidinylmethyl)piperazine;
1-[(3,4-Dichlorophenyl)acetyl]-4-(1-oxo-2-propenyl)-2-(1-pyrrolidinylmethyl)piperazine;
1-[(3,4-Dichlorophenyl)acetyl]-4-(1-oxopropyl)-2-(1-pyrrolidinylmethyl)piperazine;
4-Acetyl-1-[(3,4-dichlorophenyl)acetyl]-2-(1,2,3,6-tetrahydro-1-pyridinylmethyl)piperazine;
Ethyl 4-[(3,4-dichlorophenyl)acetyl]-3-(1-pyrrolidinylmethyl)-1-piperazinecarboxylate;
Methyl 4-[(3,4-dichlorophenyl)acetyl]-3-(1,2,3,6-tetrahydro-1-pyridinylmethyl)-1-piperazinecarboxylate; or a physiologically acceptable salt thereof.
8. Methyl 4-[(3,4-dichlorophenyl)acetyl]-3-(1-pyrrolidinylmethyl)-1-piperazinecarboxylate or a physiologically acceptable salt thereof.
9. A pharmaceutical composition for the treatment of a human suffering from pain or cerebral ischaemia which comprises an effect amount of a compound of formula (I) as defined in claim 1 or a physiologically acceptable salt thereof together with a pharmaceutically acceptable carrier thereof.
10. A method of treating a human suffering from pain or cerebral ischaemia which comprises administering an effective amount of a compound of formula (I) as defined in claim 1 or a physiologically acceptable salt thereof.

* * * * *